United States Patent [19]

Tuloup et al.

[11] Patent Number: 5,203,875
[45] Date of Patent: Apr. 20, 1993

[54] DYEING COMPOSITION FOR KERATINOUS FIBERS, CONTAINING OXIDATION DYE PRECURSORS AND HYDROXYBENZOFURANE USED AS COUPLERS, AND DYEING PROCESS USING THESE COMPOSITIONS

[75] Inventors: Remy Tuloup, Miniac-sous-Bécherel; Christian Blaise, Sevran; Alex Junino, Livry-Gargan, all of France

[73] Assignee: L'Oreal, Paris, France

[21] Appl. No.: 860,543

[22] Filed: Mar. 30, 1992

[30] Foreign Application Priority Data

Mar. 28, 1991 [FR] France ................... 91 03806

[51] Int. Cl.$^5$ ............................................. A61K 7/13
[52] U.S. Cl. ........................................ 8/405; 8/406; 8/407; 8/408; 8/414; 8/416; 8/421; 8/423; 424/70
[58] Field of Search ............... 8/405, 406, 407, 408, 8/414, 416, 421, 423; 424/70

[56] References Cited

U.S. PATENT DOCUMENTS 4,620,850 11/1986 Bachmann et al. ................... 8/406

FOREIGN PATENT DOCUMENTS 0023080 1/1981 European Pat. Off. .
0026474 4/1981 European Pat. Off. .
2410634 9/1975 Fed. Rep. of Germany .
2719424 11/1978 Fed. Rep. of Germany .

OTHER PUBLICATIONS

Chemical Abstracts, L. Rene, et al. Dec. 10, 1973, vol. 79, No. 23.

*Primary Examiner*—Paul Lieberman
*Assistant Examiner*—William S. Parks
*Attorney, Agent, or Firm*—Jacobson, Price, Holman & Stern

[57] ABSTRACT

The invention relates to the use, as coupler in a dyeing composition, of a hydroxybenzofuran of formula (I):

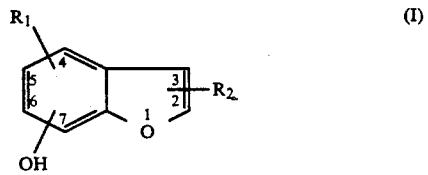

in which $R_1$ and $R_2$, which are identical or different, represent a hydrogen atom or a $C_1$-$C_6$ alkyl radical. When they denote an alkyl radical, $R_1$ and $R_2$ can occupy any position on the benzofuran ring except the positions 2 and 3 at the same time. The OH group may occupy one of the positions 4, 5, 6 or 7, in combination with one or more para type or ortho type oxidation dye precursors or mixtures thereof, for dyeing keratinous fibers and in particular human hair. The dyeing composition according to the invention makes it possible to confer on the keratinous fibers a color which is fast to light, washes, adverse weather conditions and perspiration.

18 Claims, No Drawings

DYEING COMPOSITION FOR KERATINOUS FIBERS, CONTAINING OXIDATION DYE PRECURSORS AND HYDROXYBENZOFURANE USED AS COUPLERS, AND DYEING PROCESS USING THESE COMPOSITIONS

The present invention relates to novel dyeing compositions for keratinous fibers and in particular for human hair, containing oxidation dye precursors and hydroxybenzofurans used as couplers and a dyeing process using such compositions.

The dyeing of keratinous fibers and in particular human hair with dyeing compositions containing oxidation dye precursors and in particular ortho- or para-phenylenediamines, ortho- or para-aminophenols, generally called "oxidation bases", is known.

It is also known that the shades obtained with these oxidation bases may be varied by combining them with couplers also called color modifiers, chosen in particular from aromatic meta-diamines, meta-aminophenols and meta-diphenols.

Oxidation dye precursors or couplers which make it possible to confer on hair, in an oxidizing alkaline or acid medium, a color having satisfactory fastness to light, washes, adverse weather conditions and perspiration, are sought in the field of hair dyeing.

The Applicant has just discovered, and this constitutes the subject of the invention, that the use of 4-, 5-, 6- or 7-hydroxybenzofurans as couplers, with oxidation dye precursors, made it possible to obtain, after application to keratinous fibers and in particular to hair, dyeings exhibiting particularly remarkable fastness to light, washes, adverse weather conditions and perspiration, in particular when they are used with p-phenylenediamine and its derivatives.

One subject of the invention therefore consists of oxidation dyeing compositions, intended to be used for dyeing keratinous fibers, containing at least one para and/or ortho type oxidation dye precursor with certain hydroxybenzofurans defined below.

Another subject of the invention consists of the process for dyeing keratinous fibers, in particular human hair, using such compositions.

Other subjects of the invention will emerge from reading the following description and examples.

The oxidation dyeing composition conforming to the invention, which is intended to be used for dyeing keratinous fibers and in particular human hair, is essentially characterized in that it contains in a medium suitable for dyeing, at least one para and/or ortho oxidation dye precursor and at least one heterocyclic coupler of the formula (I):

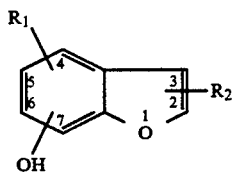

(I)

in which $R_1$ and $R_2$, which are identical or different, represent a hydrogen atom or a $C_1$–$C_6$ alkyl radical. $R_1$ and $R_2$ can occupy any position on the benzofuran ring. However, when $R_1$ and $R_2$ both denote an alkyl radical, they do not occupy the positions 2 and 3 at the same time. The OH group can occupy one of the positions 4, 5, 6 or 7.

The following should be mentioned among the preferred meanings of the alkyl radical: methyl, ethyl, propyl, isopropyl, butyl, isobutyl, tert-butyl, pentyl and hexyl.

These compounds and the process for their preparation are known.

However, their use as coupler in a dyeing composition in combination with one or more oxidation dye precursors is new.

The article by Loïc RENE and René ROYER in Bulletin de la Société Chimique de France, 1973, 2355–2356, describes the preparation of hydroxybenzofurans.

The book "Heterocyclic Compounds", Volume 29, Benzofurans (1974) by MUSTAFA, publisher: WILEY INTER-SCIENCE, describes the preparation of hydroxybenzofurans and substituted hydroxybenzofurans.

Among the substituted hydroxybenzofurans of formula (I), the following should be mentioned more particularly:
2-methyl-6-hydroxybenzofuran,
3-methyl-6-hydroxybenzofuran,
2,4-dimethyl-6-hydroxybenzofuran,
3-n-propyl-6-hydroxybenzofuran,
2-ethyl-5-hydroxybenzofuran,
2-methyl-5-hydroxybenzofuran,
3-methyl-5-hydroxybenzofuran,
3-isobutyl-5-hydroxybenzofuran,
3-ethyl-5-hydroxybenzofuran,
2,6-dimethyl-5-hydroxybenzofuran,
3,6-dimethyl-5-hydroxybenzofuran,
6,7-dimethyl-5-hydroxybenzofuran,
3-n-propyl-5-hydroxybenzofuran,
3-methyl-4-n-propyl-5-hydroxybenzofuran,
2-hexyl-5-hydroxybenzofuran,
2-n-propyl-5-hydroxybenzofuran,
4-tert-butyl-5-hydroxybenzofuran,
6-tert-butyl-5-hydroxybenzofuran,
4-methyl-5-hydroxybenzofuran,
3-isobutyl-5-hydroxybenzofuran,
3-methyl-5-n-propyl-4-hydroxybenzofuran,
2-ethyl-4-hydroxybenzofuran,
2-methyl-6-pentyl-4-hydroxybenzofuran,
6-pentyl-4-hydroxybenzofuran,
3,5-dimethyl-4-hydroxybenzofuran,
3,7-dimethyl-4-hydroxybenzofuran,
2,6-di-tert-butyl-4-hydroxybenzofuran,
2-methyl-4-hydroxybenzofuran,
3-methyl-4-hydroxybenzofuran,
2-methyl-7-ethyl-4-hydroxybenzofuran,
2,7-dimethyl-4-hydroxybenzofuran,
2-isopropyl-4-hydroxybenzofuran,
3-ethyl-4-hydroxybenzofuran,
3-methyl-7-tert-butyl-4-hydroxybenzofuran,
3-methyl-5-tert-butyl-4-hydroxybenzofuran,
2,6-dimethyl-4-hydroxybenzofuran,
3-isopropyl-4-hydroxybenzofuran,
3-n-propyl-4-hydroxybenzofuran,
3-methyl-7-n-propyl-4-hydroxybenzofuran,
3-methyl-6-n-propyl-7-hydroxybenzofuran,
3-methyl-7-hydroxybenzofuran,
2-ethyl-4-methyl-7-hydroxybenzofuran,
2-ethyl-5-methyl-7-hydroxybenzofuran.

The para or ortho type oxidation dye precursors are compounds which are not dyes themselves, but which form a dye by a process of oxidative condensation, either by themselves or in the presence of a coupler or a modifier.

These compounds contain functional groups, either two amino, or an amino and a hydroxyl, in the para or ortho position with respect to each other.

The para type oxidation dye precursors are in particular chosen from para-phenylenediamines, para-aminophenols, para-heterocyclic precursors such as 2,5-diaminopyridine, 2-hydroxy-5-aminopyridine, tetraaminopyrimidine, and so-called "double" bases.

As para-phenylenediamines, the compounds of formula (II) below may be mentioned:

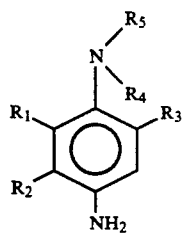

(II)

in which $R_1$, $R_2$ and $R_3$, which are identical or different, represent a hydrogen or halogen atom, an alkyl radical having 1 to 4 carbon atoms, an alkoxy radical having 1 to 4 carbon atoms, $R_4$ and $R_5$, which are identical or different, represent a hydrogen atom, an alkyl, hydroxyalkyl, alkoxyalkyl, carbamylalkyl, mesylaminoalkyl, acetylaminoalkyl, ureidoalkyl, carbalkoxyaminoalkyl, piperidinoalkyl, morpholinoalkyl or phenyl radical optionally substituted in the para position by an amino group, these alkyl or alkoxy groups having 1 to 4 carbon atoms, or alternatively $R_4$ and $R_5$ form, together with the nitrogen atom to which they are attached, a piperidino or morpholino heterocycle, provided that $R_1$ or $R_3$ represents a hydrogen atom when $R_4$ and $R_5$ do not represent a hydrogen atom, as well as the salts of these compounds.

Among the compounds of formula (II), there may be mentioned p-phenylenediamine, p-tolylenediamine, methoxypara-phenylenediamine, chloro-para-phenylenediamine, 2,6-dimethyl-para-phenylenediamine, 2,6-diethyl-para-phenylenediamine, 2,5-dimethyl-para-phenylenediamine, 2-methyl-5-methoxy-para-phenylenediamine, 2,6-dimethyl-5-methoxypara-phenylenediamine, N,N-dimethyl-para-phenylenediamine, N,N-diethyl-para-phenylenediamine, N,N-dipropyl-para-phenylenediamine, 3-methyl-4-amino-N,N-diethylaniline, N,N-di($\beta$-hydroxyethyl)-para-phenylenediamine, 3-methyl-4-amino-N,N-di ($\beta$-hydroxyethyl)aniline, 3-chloro-4-amino-N,N-di($\beta$-hydroxyethyl)aniline, 4-amino-N-ethyl-N-carbamylmethylaniline,3-methyl-4-amino-N-ethyl-N-carbamylmethylaniline, 4-amino-N-ethyl-N-$\beta$-piperidinoethylaniline, 3-methyl-4-amino-N-ethyl-N-$\beta$-piperidinoethylaniline, 4-amino-N-ethyl-N-$\beta$-morpholinoethylaniline, 3-methyl-4-amino-N-ethyl-N-$\beta$-morpholinoethylaniline, 4-amino-N-ethyl-N-$\beta$-acetylaminoethylaniline, 4-amino-N-($\beta$-methoxyethyl)aniline, 3-methyl-4-amino-N-ethyl-N-$\beta$-acetylaminoethylmethyl-4-amino-N-ethyl-N-$\beta$-mesylaminoethylaniline, 3-methyl-4-amino-N-ethyl-N-$\beta$-mesylaminoethylaniline, 4-amino-N-ethyl-N-$\beta$-sulfoethylaniline, 3-methyl-4-amino-N-ethyl-N-$\beta$-sulfoethylaniline, N-[(4'-amino)phenyl]-morpholine, N-[(4'-amino)phenyl]piperidine, 2-hydroxyethyl-para-phenylenediamine, fluoro-para-phenylenediamine, carboxy-para-phenylenediamine, sulfo-para-phenylenediamine, 2-isopropyl-para-phenylenediamine, 2-n-propyl-para-phenylenediamine, hydroxy-2-n-propyl-para-phenylenediamine, 2-hydroxymethyl-para-phenylenediamine, N,N-dimethyl-3-methyl-para-phenylenediamine, N-ethyl-N-$\beta$-hydroxyethyl-para-phenylenediamine, N-(dihydroxypropyl)para-phenylenediamine, N-4'-aminophenyl-para-phenylenediamine, N-phenyl-para-phenylenediamine.

These para type oxidation dye precursors may be introduced into the dyeing composition either in the form of a free base or in the form of salts, such as hydrochloride, hydrobromide or sulfate.

Among the p-aminophenols, there may be mentioned p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2-hydroxymethyl-4-aminophenol, 2-($\beta$-hydroxyethyl)-4-aminophenol, 2-methoxy-4-aminophenol, 3-methoxy-4-aminophenol, 2,5-dimethyl-4-aminophenol, 2-methoxymethyl-4-aminophenol, 2-aminomethyl-4-aminophenol and 2-$\beta$-hydroxyethylaminomethyl-4-aminophenol.

The ortho type oxidation dye precursors are chosen from ortho-aminophenols such as 1-amino-2-hydroxybenzene, 6-methyl-1-hydroxy-2-aminobenzene, 4-methyl-1-amino-2-hydroxybenzene and ortho-phenylenediamines.

The so-called double bases are bis-phenylenealkylenediamines of the formula:

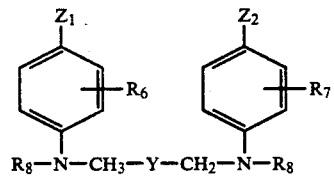

(III)

$R_8-N-CH_3-Y-CH_2-N-R_8$ in which:

$Z_1$ and $Z_2$, which are identical or different, represent hydroxyl or $NHR_9$ groups, where $R_9$ denotes a hydrogen atom or a lower alkyl radical;

$R_6$ and $R_7$, which are identical or different, represent hydrogen atoms, halogen atoms or alternatively alkyl groups;

$R_8$ represents a hydrogen atom, an alkyl or hydroxyalkyl group, or an aminoalkyl group whose amino residue may be substituted by one or two alkyl groups;

Y represents a radical chosen from the following radicals:

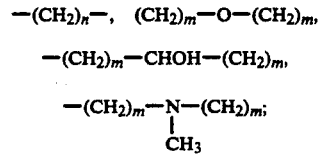

n is an integer between 0 and 8 and m is an integer between 0 and 4. These so-called double bases may also exist in the form of their addition salts with acids.

The alkyl or alkoxy radicals indicated above preferably denote a group having 1 to 4 carbon atoms and preferably methyl, ethyl, propyl, methoxy or ethoxy.

Among the compounds of formula (III), there may be mentioned N,N'-bis($\beta$-hydroxyethyl)-N,N'-bis(4,-aminophenyl)-1,3-diamino-2-propanol, N,N'-bis($\beta$-hydroxyethyl)N,N'-bis(4'-aminophenyl)ethylenediamine, N,N'-bis(4-aminophenyl)tetramethylenediamine, N,N'-bis($\beta$-hydroxyethyl)N,N'-bis(4-aminophenyl)tetramethylenediamine, N,N'-bis(4-methylaminophenyl)tetramethylenediamine, N,N'-bis-(ethyl)-N,N'-bis(4'-amino-3'-methylphenyl)ethylenediamine.

The dyeing compositions may also contain, in addition to the heterocyclic coupler of the family of hydroxybenzofurans of formula (I) defined above, other couplers known per se, such as meta-diphenols, meta-aminophenols, meta-phenylenediamines, meta-acylaminophenols, meta-ureidophenols, meta-carbalkoxyaminophenols, $\alpha$-naphthol, couplers containing an active methylene group such as $\beta$-ketonic compounds, pyrazolones, heterocyclic couplers and 4-, 6- or 7-hydroxyindole.

Among these couplers, there may be mentioned more particularly 2,4-dihydroxyphenoxyethanol, 2,4-dihydroxyanisole, meta-aminophenol, resorcinol monomethyl ether, 2-methyl-5-N-($\beta$-hydroxyethyl)aminophenol, 2-methyl-5-N-($\beta$-mesylaminoethyl)aminophenol, 6-hydroxybenzomorpholine, 2,4-diaminoanisole, 2,4-diaminophenoxyethanol, 6-aminobenzomorpholine, [2-N-($\beta$-hydroxyethyl)amino-4-amino]-phenoxyethanol,2-amino-4-N-($\beta$-hydroxyethyl)aminoanisole, (2,4-diamino)phenyl-$\beta$,$\gamma$-dihydroxypropyl ether, 2,4-diaminophenoxyethylamine, 1,3-dimethoxy-2,4-diaminobenzene, 2-methyl-5-aminophenol, 2,6-dimethyl-3-aminophenol, 1-amino-3,4-methylenedioxybenzene, 1-hydroxy-3,4-methylenedioxybenzene, 2-chloro-6-methyl-3-aminophenol, 2-methyl3-aminophenol, 2-chlororesorcinol, resorcinol, 6-methoxy-3-hydroxyethylaminoaniline, 1-ethoxy-2-bis($\beta$-hydroxyethyl)amino-4-aminobenzene, 3-diethylaminophenol, 1,3-dihydroxy-2-methylbenzene, 1-hydroxy-2,4-dichloro-3-aminobenzene, 4,6-hydroxyethoxy-1,3-diaminobenzene, 4-methyl-6-ethoxy-1,3-diaminobenzene, 4-chloro-6-methyl-3-aminophenol, 6-chloro-3-trifluoroethylaminophenol.

Direct dyes such as azo or anthraquinone dyes or the nitro derivatives of the benzene series may be added to these compositions, as it is well known in the state of the art, in particular in order to impart a shade to or increase the shimmer of the colors provided by the oxidation dye precursors and the coupler of formula (I).

The para and/or ortho type oxidation dye precursors as a whole, as well as the couplers used in the dyeing compositions conforming to the invention, represent preferably 0.3 to 7% by weight relative to the weight of the said composition. The concentration of hydroxybenzofurans of formula (I) is 0.05 to 3.5% by weight of the total weight of the composition.

The medium suitable for dyeing generally consists of an aqueous medium and its pH may range between 4 and 11.

The dyeing compositions conforming to the invention also contain, in the preferred embodiment thereof, anionic, cationic, nonionic or amphoteric surface-active agents or mixtures thereof.

These surface-active agents are present in the compositions conforming to the invention in proportions of between 0.5 and 55% by weight, and preferably between 2 and 50% by weight relative to the total weight of the composition.

These compositions may also contain organic solvents for solubilizing compounds which might not be sufficiently soluble in water. Among these solvents, there may be mentioned by way of example, lower $C_1$-$C_4$ alkanols such as ethanol and isopropanol; glycerol; glycols or glycol ethers such as 2-butoxyethanol, ethylene glycol, propylene glycol, diethylene glycol monoethyl ether and diethylene glycol monomethyl ether, as well as aromatic alcohols such as benzyl alcohol or phenoxyethanol, similar products and mixtures thereof.

The solvents, are present, preferably, in proportions of between 1 and 40% by weight, and in particular between 5 and 30% by weight relative to the total weight of the composition.

The thickening agents which may be added to the compositions conforming to the invention may be chosen from sodium alginate, gum arabic, cellulose derivatives, acrylic acid polymers, xanthan gum, scleroglucans. Inorganic thickening agents such as bentonite may also be used.

These thickening agents are present, preferably, in proportions between 0.1 and 5%, and in particular between 0.2 and 3% by weight relative to the total weight of the composition.

The antioxidants which may be present in the compositions are chosen in particular from sodium sulfite, thioglycolic acid, sodium bisulfite, dehydroascorbic acid, hydroquinone and homogentisic acid. These antioxidants are present in the composition in proportions of between 0.5 and 1.5% by weight relative to the total weight of the composition. These compositions may also contain other cosmetically acceptable adjuvants such as for example penetrating agents, sequestering agents, perfumes, buffers, alkaline agents and propellants.

The compositions conforming to the invention may be provided in various forms, such as in the form of liquids, creams, gels or in any other form suitable for carrying out dyeing of keratinous fibers and in particular of human hair. These compositions may be packaged in aerosol cans in the presence of a propelling agent.

The dyeing compositions conforming to the invention, containing a para type or ortho type oxidation dye precursor or mixture thereof and one or more hydroxybenzofurans of formula (I) serving as coupler, are used in the processes for dyeing keratinous fibers and in particular human hair, according to a process in which the developing is carried out using an oxidizing agent.

In accordance with this process, the dyeing composition described above is mixed at the time of use with an oxidizing solution in an amount which is sufficient in order to be able to develop a color, and the mixture obtained is then applied to the keratinous fibers and in particular human hair.

The pH of the composition applied to the hair ranges between 3.5 and 10.

The oxidizing solution contains by way of oxidizing agent, hydrogen peroxide, urea peroxide, persalts such as ammonium persulfate, or alkali metal bromates. A solution of hydrogen peroxide at 20 volumes (6% by weight) is preferably used. The mixture obtained is applied to the hair and allowed to act for 10 to 40 minutes, preferably 15 to 30 minutes, after which the hair is rinsed, washed with shampoo, rinsed again and dried.

The heterocyclic coupler of the family of hydroxybenzofurans of formula (I) defined above may also be used in a multistage process consisting, in one of the stages, in applying to the keratinous fibers a dyeing composition containing the para type or ortho type oxidation dye precursor or mixture thereof and, in another stage, in applying a dyeing composition containing the coupler of formula (I), the oxidizing agent being introduced, just before application, into the composition applied in the second stage, or alternatively it is applied to the keratinous fibers in a third stage, the exposure, drying and washing conditions being similar to those indicated above.

The invention will be best understood with the aid of the non-restrictive examples below.

EXAMPLES OF APPLICATION

EXAMPLES 1 TO 4

Oxidation Dyeing at Acidic pH

The following composition is prepared:

| | |
|---|---|
| polyglycerolated oleyl alcohol containing 2 moles of glycerol | 4.0 g |
| polyglycerolated oleyl alcohol containing 4 moles of glycerol and 78% of AI | 5.69 g AI |
| oleic acid | 3.0 g |
| oleylamine containing 2 moles of ethylene oxide sold under the name ETHOMEEN O 12 by ARMAK | 7.0 g |
| diethylaminopropyl lauryl aminosuccinamate, sodium salt containing 55% of AI | 3.0 g AI |
| oleyl alcohol | 5.0 g |
| oleic acid diethanolamide | 12.0 g |
| propylene glycol | 3.5 g |
| ethyl alcohol | 7.0 g |
| dipropylene glycol | 0.5 g |
| propylene glycol monomethyl ether | 9.0 g |
| sodium metabisulfite in aqueous solution containing 35% of AI | 0.45 g AI |
| ammonium acetate | 0.8 g |
| antioxidant qs | |
| sequestrant qs | |
| perfume qs | |
| preservatives qs | |
| monoethanolamine qs pH = 9.8 | |
| dyes | x g |
| deionized water qs | 100.0 g |

AI = active ingredient

The above composition is mixed, weight for weight, with hydrogen peroxide at 20 volumes (6% by weight) whose pH is adjusted to between 1 and 1.5 with 2.5 g of orthophosphoric acid.

This mixture has a pH of about 6.5.

The mixture is applied either to natural gray hair which is 90% white (N) or to permanent-waved gray hair which is 90% white (P) in an amount of 28 g of mixture per 3 g of hair. The mixture is allowed to act for 30 minutes. The hair is then rinsed with water and washed with a shampoo and then dried.

The weight x of dyes (hydroxybenzofurans of formula (I) and oxidation dye precursor) and the colors obtained are collated in Table (I) below:

TABLE I

| DYES | EX. 1 | EX. 2 | EX. 3 | EX. 4 |
|---|---|---|---|---|
| 4-hydroxy-benzofuran | 0.402 g | | | |
| 5-hydroxy-benzofuran | | 0.402 g | | |
| 6-hydroxy-benzofuran | | | 0.402 g | |
| 7-hydroxy-benzofuran | | | | 0.402 g |
| 2,6-dimethyl-p-phenylene-diamine | 0.627 g | | | 0.627 g |
| p-phenylene-diamine | | 0.324 g | 0.324 g | |
| color obtained on natural hair (N) | dull blue ashen | | very dull golden ashen dark blond | |
| color obtained on permanent-waved hair (P) | | dull ashen auburn | | dull ashen |

EXAMPLES 5 TO 7

Oxidation Dyeing at Basic pH

The following composition is prepared:

| | |
|---|---|
| octyldodecanol sold under the name EUTANOL G by HENKEL | 8.0 g |
| oleic acid | 20.0 g |
| monoethanolamine lauryl ether sulfate sold under the name SIPON LM 35 by HENKEL | 3.0 g |
| ethyl alcohol | 10.0 g |
| benzyl alcohol | 10.0 g |
| cetylstearyl alcohol containing 33 moles of ethylene oxide sold under the name SIMULSOL GS by SEPPIC | 2.4 g |
| ethylenediaminetetraacetic acid | 0.2 g |
| aqueous solution containing 60% of AI of a cationic polymer containing units of formula: | 3.7 g |

$$\left[\begin{array}{cc} CH_3 \;\; Cl^{\ominus} & CH_3 \;\; Cl^{\ominus} \\ | & | \\ -N^{\oplus}-(CH_2)_3-N^{\oplus}-(CH_2)_6- \\ | & | \\ CH_3 & CH_3 \end{array}\right]$$

| | |
|---|---|
| monoethanolamine | 7.5 g |
| linoleic acid diethanolamide sold under the name COMPERLAN F by HENKEL | 8.0 g |
| ammonium hydroxide containing 20% of NH$_3$ | 10.2 g |
| sodium metabisulfite in aqueous solution at 35% | 1.3 g |
| hydroquinone | 0.15 g |
| 1-phenyl-3-methyl-5-pyrazolone | 0.2 g |
| dyes | x g |
| deionized water | qs 100.0 g |

The above composition is mixed, weight for weight, with hydrogen peroxide at 20 volumes (6% by weight) whose pH is equal to 3. The mixture thus prepared has a pH of about 9.5 and it is applied either to natural gray hair which is 90% white (N) or to permanent-waved gray hair which is 90% white (P), in an amount of 28 g of mixture per 3 of hair. The mixture is allowed to act for 30 minutes. The hair is then rinsed with water, washed with a shampoo and then dried.

The colors obtained are collated in Table (II) below.

TABLE II

| DYES | EXAMPLE 5 | EXAMPLE 6 | EXAMPLE 7 |
|---|---|---|---|
| 4-hydroxy-benzofuran | 0.536 g | | |
| 6-hydroxy-benzofuran | | 0.268 g | |
| 7-hydroxy-benzofuran | | | 0.268 g |
| p-aminophenol | 0.436 g | | |
| p-phenylene-diamine | | 0.216 g | 0.216 g |

TABLE II-continued

| DYES | EXAMPLE 5 | EXAMPLE 6 | EXAMPLE 7 |
|---|---|---|---|
| Color obtained on natural hair (N) | very pearly light blond | dull ashen natural light blond | |
| color obtained on permanent-waved hair (P) | | | pinkish beige |

EXAMPLE 8

Acidic Oxidation Dyeing

The following composition is prepared:

| | |
|---|---|
| polyglycerolated oleyl alcohol containing 2 moles of glycerol | 4.0 g |
| polyglycerolated oleyl alcohol containing 4 moles of glycerol and 78% of AI | 5.69 g AI |
| oleic acid | 3.0 g |
| oxyethyleneated oleylamine containing 2 moles of ethylene oxide sold under the name ETHOMEEN O 12 by AKZO | 7.0 g |
| diethylaminopropyl lauryl aminosuccinamate, sodium salt containing 55% of AI | 3.0 g AI |
| oleyl alcohol | 5.0 g |
| oleic acid diethanolamide | 12.0 g |
| propylene glycol | 3.5 g |
| ethyl alcohol | 7.0 g |
| dipropylene glycol | 0.5 g |
| propylene glycol monomethyl ether | 9.0 g |
| sodium metabisulfite in aqueous solution containing 35% of AI | 0.45 g AI |
| ammonium acetate | 0.8 g |
| antioxidant qs | |
| sequestrant qs | |
| perfume qs | |
| preservative qs | |
| monoethanolamine qs pH = 9.8 | |
| 3-methyl-6-hydroxybenzofuran | 0.45 g |
| 2,6-dimethyl-p-phenylenediamine dihydrochloride | 0.63 g |
| deionized water qs | 100.0 g |

The composition obtained is mixed, weight by weight, with hydrogen peroxide at 20 volumes, whose pH is adjusted to between 1 and 1.5 with phosphoric acid (2.5 g of phosphoric acid per 100 g of hydrogen peroxide).

The mixture thus prepared has a pH of about 6.5. It is applied to permanent-waved gray hair for 30 minutes at room temperature. After rinsing and washing, the hair is dyed in dull golden blond.

EXAMPLES 9 TO 10

Alkaline Oxidation Dyeing

The following compositions are prepared:

| | |
|---|---|
| octyldodecanol sold under the name EUTANOL D by HENKEL | 8.0 g |
| oleic acid | 20.0 g |
| monoethanolamine lauryl ether sulfate sold under the name SIPON LM 35 by HENKEL | 3.0 g |
| ethyl alcohol | 10.0 g |
| benzyl alcohol | 10.0 g |
| cetylstearyl alcohol containing 33 moles of ethylene oxide sold under the name SIMULSOL GS by SEPPIC | 2.4 g |
| ethylenediaminetetraacetic acid | 0.2 g |
| aqueous solution containing 60% of AI of a cationic polymer containing units of formula: | 3.7 g |

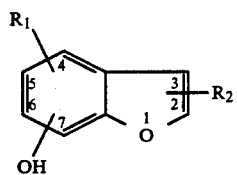

| | |
|---|---|
| monoethanolamine | 7.5 g |
| linoleic acid diethanolamide sold under the name COMPERLAN F by HENKEL | 8.0 g |
| ammonium hydroxide containing 20% of NH$_3$ | 10.2 g |
| sodium metabisulfite in aqueous solution at 35% | 1.3 g |
| hydroquinone | 0.15 g |
| 1-phenyl-3-methyl-5-pyrazolone | 0.2 g |
| hydroxybenzofurans and oxidation dye precursors indicated in the table | |
| deionized water | qs 100.0 g |

The composition obtained is mixed, weight for weight, with hydrogen peroxide at 20 volumes and whose pH is equal to 3. The mixture has a pH of about 09.5. It is applied to permanent-waved gray hair for 30 minutes. After rinsing and washing, the hair is dyed in the color indicated in the table.

| Examples | Hydroxybenzofurans and dye precursors | | Color of the dyed hair |
|---|---|---|---|
| 9 | 3-methyl-6-hydroxy-benzofuran | 0.30 g | ashen natural |
| | p-phenylenediamine | 0.22 g | blond |
| 10 | 3-methyl-6-hydroxy-benzofuran | 0.89 g | dull golden |
| | p-phenylenediamine | 0.92 g | light blond |

We claim:

1. A dyeing composition for dyeing keratinous fibers and in particular human hair, which comprises, as coupler in an aqueous or dilute alcoholic vehicle, one or more hydroxybenzofurans of formula (I):

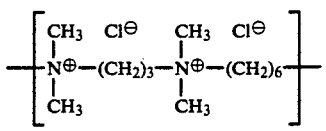

in which R$_1$ and R$_2$, which are identical or different, represent a hydrogen atom or a C$_1$-C$_6$ alkyl radical, R$_1$ and R$_2$ can occupy any position on the benzofuran ring provided that when R$_1$ and R$_2$ both denote an alkyl radical, they do not occupy the positions 2 and 3 at the same time, the concentration of the hydroxybenzofurans of formula (I) being 0.05 to 3.5% by weight of the total weight of the composition, in combination with one or more oxidation dye precursors selected form the group consisting of a para-phenylenediamine, a para-aminophenol, 2,5-diaminopyridine, 2-hydroxy-5-aminopyridine, tetraaminopyrimidine, 1-amino-2-hydroxybenzene, 6-methyl-1-hydroxy-2-aminobenzene, 4-methyl-1-amino-2-hydroxybenzene, an ortho-phenylenediamine and a bis-phenylenealkylenediamine of formula (III) and their addition salts with acids:

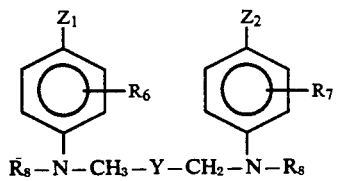

in which:

Z$_1$ and Z$_2$, which are identical or different, represent a hydroxyl or NHR$_9$ groups, where R$_9$ denotes a hydrogen atom or a lower alkyl radical;

R$_6$ and R$_7$, which are identical or different, represent a hydrogen atom, a halogen atom or an alkyl group;

R$_8$ represents a hydrogen atom, an alkyl or hydroxyalkyl group, or an aminoalkyl group which amino residue is unsubstituted or substituted by one or two alkyl groups;

Y represents a radical selected from the group of radicals consisting of:

$$-(CH_2)_n-, (CH_2)_m-O-(CH_2)_m,$$
$$-(CH_2)_m-CHOH-(CH_2)_m, \text{ and}$$
$$-(CH_2)_m-\underset{\underset{CH_3}{|}}{N}-(CH_2)_m;$$

in which n is an integer between 0 and 8 and m is an integer between 0 and 4, and in which the alkyl or alkoxy radicals indicated above denote a group having 1 to 4 carbon atoms or mixtures thereof.

2. The dyeing composition as claimed in claim 1, wherein the hydroxybenzofuran of formula (I) is chosen from the following group:

2-methyl-6-hydroxybenzofuran,
3-methyl-6-hydroxybenzofuran,
2,4-dimethyl-6-hydroxybenzofuran,
3-n-propyl-6-hydroxybenzofuran,
2-ethyl-5-hydroxybenzofuran,
2-methyl-5-hydroxybenzofuran,
3-methyl-5-hydroxybenzofuran,
3-isobutyl-5-hydroxybenzofuran,
3-ethyl-5-hydroxybenzofuran,
2,6-dimethyl-5-hydroxybenzofuran,
3,6-dimethyl-5-hydroxybenzofuran,
6,7-dimethyl-5-hydroxybenzofuran,
3-n-propyl-5-hydroxybenzofuran,
3-methyl-4-n-propyl-5-hydroxybenzofuran,
2-hexyl-5-hydroxybenzofuran,
2-n-propyl-5-hydroxybenzofuran,
4-tert-butyl-5-hydroxybenzofuran,
6-tert-butyl-5-hydroxybenzofuran,
4-methyl-5-hydroxybenzofuran,
3-isobutyl-5-hydroxybenzofuran,
3-methyl-5-n-propyl-4-hydroxybenzofuran,
2-ethyl-4-hydroxybenzofuran,
2-methyl-6-pentyl-4-hydroxybenzofuran,
6-pentyl-4-hydroxybenzofuran,
3,5-dimethyl-4-hydroxybenzofuran,
3,7-dimethyl-4-hydroxybenzofuran,
2,6-di-tert-butyl-4-hydroxybenzofuran,
2-methyl-4-hydroxybenzofuran,
3-methyl-4-hydroxybenzofuran,
2-methyl-7-ethyl-4-hydroxybenzofuran,
2,7-dimethyl-4-hydroxybenzofuran,
2-isopropyl-4-hydroxybenzofuran,
3-ethyl-4-hydroxybenzofuran,
3-methyl-7-tert-butyl-4-hydroxybenzofuran,
3-methyl-5-tert-butyl-4-hydroxybenzofuran,
2,6-dimethyl-4-hydroxybenzofuran,
3-isopropyl-4-hydroxybenzofuran,
3n-propyl-4-hydroxybenzofuran,
3-methyl-7-n-propyl-4-hydroxybenzofuran,
3-methyl-6-n-propyl-7-hydroxybenzofuran,
3-methyl-7-hydroxybenzofuran,
2-ethyl-4-methyl-7-hydroxybenzofuran,
2-ethyl-5-methyl-7-hydroxybenzofuran.

3. The dyeing composition as claimed in claim 2, wherein the hydroxybenzofuran is chosen from the group consisting of 3-methyl-6-hydroxybenzofuran and 4-, 5-, 6-and 7-hydroxybenzofurans.

4. The dyeing composition as claimed in claim 1, wherein the para-phenylenediamines are of the formula:

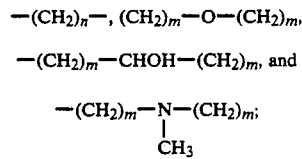

in which R$_1$, R$_2$ and R$_3$, which are identical or different, represent a hydrogen or halogen atom, an alkyl radical having 1 to 4 carbon atoms, an alkoxy radical having 1 to 4 carbon atoms, R$_4$ and R$_5$, which are identical or different, represent a hydrogen atom, an alkyl, hydroxyalkyl, alkoxyalkyl, carbamylalkyl, mesylaminoalkyl, acetylaminoalkyl, ureidoalkyl, carbalkoxyaminoalkyl, piperidinoalkyl, morpholinoalkyl or phenyl radical, or a phenyl radical substituted in the para position by an amino group, these alkyl or alkoxy groups having 1 to 4 carbon atoms, or alternatively R$_4$ and R$_5$ form, together with the nitrogen atom to which they are attached, a piperidino or morpholino heterocycle, provided that R$_1$ or R$_3$ represents a hydrogen atom when R$_4$ and R$_5$ do not represent a hydrogen atom, as well as the salts of these compounds.

5. The dyeing composition as claimed in claim 1, which contains at least one para-phenylenediamine chosen from the group consisting of p-phenylenediamine, p-tolylenediamine, methoxy-para-phenylenediamine, chloro-para-phenylenediamine, 2,6-dimethyl-para-phenylenediamine,2,6-diethyl-para-phenylenediamine, 2,5-dimethyl-para-phenylenediamine, 2-methyl-5-methoxy-para-phenylenediamine,2,6-dimethyl-5-methoxy-para-phenylenediamine, N,N-dimethyl-para-phenylenediamine, N,N-diethyl-para-phenylenediamine, N,N-dipropyl-para-phenylenediamine, 3-methyl-4-amino-N,N-diethylaniline, N,N-di($\beta$-hydroxyethyl)-para-phenylenediamine, 3-methyl-4-amino-N,N-di($\beta$-hydroxyethyl)aniline, 3-chloro-4-amino-N,N-di($\beta$-hydroxyethyl)aniline, 4-amino-N-ethyl-N-carbamylmethylaniline, 3-methyl-4-amino-N-ethyl-N-carbamylmethylaniline, 4-amino-N-ethyl-N-$\beta$-piperidinoethylaniline, 3-methyl-4-amino-N-ethyl-N-$\beta$-piperidinoethylaniline, 4-amino-N-ethyl-N-$\beta$-morpholinoethylaniline, 3-methyl-4-amino-N-ethyl-N-$\beta$-morpholinoethylaniline, 4-amino-N-ethyl-N-β-acetylaminoethylaniline, 4-amino-N-(β-methoxyethyl)aniline, 3-methyl-4-amino-N-ethyl-N-β-acetylaminoethylaniline, 4-amino-N-ethyl-N-β-mesylaminoethylaniline, 3-methyl-4-amino-N-ethyl-N-β-mesylaminoethylaniline, 4-amino-N-ethyl-N-β-sulfoethylaniline, 3-methyl-4-amino-N-ethyl-N-β-sulfoethylaniline, N-[(4'-amino)phenyl]morpholine, N-[(4'-amino)phenyl]-piperidine, 2-hydroxyethyl-para-phenylenediamine, fluoro-para-phenylenediamine, carboxy-para-phenylenediamine, sulfo-para-phenylenediamine,2-isopropyl-para-phenylenediamine, 2-n-propyl-para-phenylenediamine, hydroxy-2-n-propyl-para-phenylenediamine, 2-hydroxymethyl-para-phenylenediamine, N,N-dimethyl-3-methyl-para-phenylenediamine, N-ethyl-N-β-hydroxyethyl-para-phenylenediamine, N-(dihydroxypropyl)-para-phenylenediamine, N-4'-aminophenyl-para-phenylenediamine, N-phenyl-para-phenylendiamine, in the form of a cosmetically acceptable free base or salt.

6. The dyeing composition as claimed in claim 1, which contains at least one p-aminophenol chosen from the group consisting of p-aminophenol, 2-methyl-4-aminophenol, 3-methyl-4-aminophenol,2-chloro-4-aminophenol,3-chloro-4-aminophenol, 2,3-dimethyl-4-aminophenol, 2-hydroxymethyl-4-aminophenol, 2-(β-hydroxyethyl)-4-aminophenol, 2-methoxy-4-aminophenol, 3-methoxy-4-aminophenol, 2,5-dimethyl-4-aminophenol, 2-methoxymethyl-4-aminophenol, 2-aminomethyl-4-aminophenol and 2-β-hydroxyethylaminomethyl-4-aminophenol.

7. The dyeing composition as claimed in claim 1, wherein the so-called double bases are chosen form N,N'-bis(β-hydroxyethyl)-N,N'-bis(4'-aminophenyl)-1,3-diamino-2-propanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine.

8. The dyeing composition as claimed in claim 1, which also contains other couplers chosen from the group consisting of meta-diphenols, meta-aminophenols, meta-phenylenediamines, meta-acylaminophenols, meta-ureidophenols, meta-carbalkoxyaminophenols, α-naphthol,couplers containing an active methylene group such as β-ketonic compounds, pyrazolones, heterocyclic couplers and 4-, 6- or 7-hydroxyindole.

9. The dyeing composition as claimed in claim 8, which contains couplers chosen from the group consisting of 2,4-dihydroxyphenoxyethanol, 2,4-dihydroxyanisole, meta-aminophenol, resorcinol monomethyl ether, 2-methyl-5-N-(β-hydroxyethyl)aminophenol, 2-methyl-5-N-(β-mesylaminoethyl)aminophenol, 6-hydroxybenzomorpholine, 2,4-diaminoanisole, 2,4-diaminophenoxyethanol, 6-aminobenzomorpholine, [2-N-(β-hydroxyethyl)amino-4-amino]phenoxyethanol, 2-amino-4-N-(β-hydroxyethyl)aminoanisole, (2,4-diamino)phenyl-β,γ-dihydroxypropyl ether, 2,4-diaminophenoxyethylamine, 1,3-dimethoxy-2,4-diaminobenzene, 2-methyl-5-aminophenol, 2,6-dimethyl-3-aminophenol, 1-amino-3,4-methylenedioxybenzene, 1-hydroxy-3,4-methylenedioxybenzene, 2-chloro-6-methyl-3-aminophenol, 2-methyl-3-aminophenol, 2-chlororesorcinol, resorcinol, 6-methoxy-3-hydroxyethylaminoaniline, 1-ethoxy-2-bis(β-hydroxyethyl)amino-4-aminobenzene, 3-diethylaminophenol, 1,3-dihydroxy-2-methylbenzene, 1-hydroxy-2,4-dichloro-3-aminobenzene, 4,6-hydroxyethoxy-1,3-diaminobenzene, 4-methyl-6-ethoxy-1,-diaminobenzene, 4-chloro-6-methyl-3-aminophenol, 6-chloro-4-trifluoroethylaminophenol, the salts and mixtures thereof.

10. The dyeing composition as claimed in claim 1, wherein the total concentration of couplers and of said oxidation dye precursors is 0.3 to 7% by weight of the total weight of the composition.

11. The dyeing composition as claimed in claim 1, which contains, in addition, direct dyes chosen from azo and anthraquinone dyes, and nitro derivatives of the benzene series.

12. The dyeing composition as claimed in claim 1, which has a pH of between 4 and 11.

13. The dyeing composition as claimed in claim 1, which contains 1 to 40% by weight of an organic solvent chosen from lower $C_1$–$C_4$ alkanols, glycerol, glycols, glycol ethers, aromatic alcohols such as benzyl alcohol or phenoxyethanol and mixtures thereof.

14. The dyeing composition as claimed in claim 1, which also contains 0.5 to 55% by weight of one or more anionic, cationic, nonionic or amphoteric surface-active agents or mixtures thereof.

15. The dyeing composition as claimed in claim 1, which contains, in addition, cosmetic adjuvants chosen from thickeners, antioxidants, penetrating agents, sequestering agents, buffers, perfumes, alkalinizing agents and propellants.

16. The dyeing composition as claimed in claim 1, which is provided in the form of liquids, creams, gels or packaged as an aerosol in the presence of a propelling agent.

17. A process for dyeing hair, by oxidation, which comprises mixing at the time of use a dyeing composition as claimed in claim 1, with an oxidizing solution in an amount which is sufficient to bring about the oxidation of the oxidation dye precursor(s), the pH of the mixture being between 3.5 and 10, and then applying the mixture obtained to hair, allowing it to act for 10 to 40 minutes, and then rinsing the hair, washing it with shampoo, rinsing it again and drying it.

18. A process for dyeing hair, by oxidation, in several stages, which comprises, in one of the stags, in applying to the hair a dyeing composition containing one or more oxidation dye precursors selected from the group consisting of a para-phenylenediamine, a para-aminophenol, 2,5-diaminopyridine, 2-hydroxy-5-aminopyridine, tetraaminopyrimidine, 1-amino-2-hydroxybenzene, 6-methyl-1-hydroxy-2-aminobenzene, 4-methyl-1-amino-2-hydroxybenzene, an ortho-phenylenediamine and a bisphenylenealkylenediamine of formula (III) and their addition salts with acids:

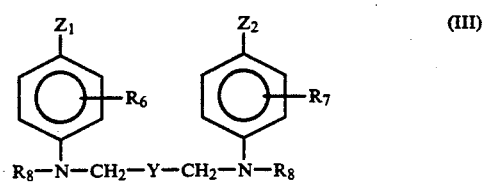

(III)

in which:
$Z_1$ and $Z_2$, which are identical or different, represent a hydroxyl or $NHR_9$ groups, where $R_9$ denotes a hydrogen atom or a lower alkyl radical;

$R_6$ and $R_7$, which are identical or different, represent a hydrogen atom, a halogen atom or an alkyl group;

$R_8$ represents a hydrogen atom, an alkyl or hydroxyalkyl group, or an aminoalkyl group whose amino residue is unsubstituted or substituted by one or two alkyl groups;

Y represents a radical selected from the group of radicals consisting of:

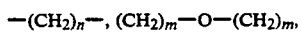

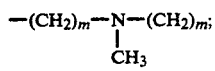

in which n is an integer between 0 and 8 and m is an integer between 0 and 4, and in which the alkyl or alkoxy radicals indicated above denote a group having 1 to 4 carbon atoms or mixtures thereof, and then, in another stage, applying a dyeing composition containing, as coupler in an aqueous or dilute alcoholic vehicle, one or more hydroxybenzofurans of formula (I):

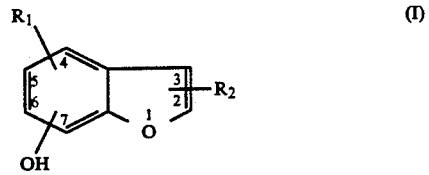

or one of its salts in which $R_1$ and $R_2$, which are identical or different, represent a hydrogen atom or a $C_1$-$C_6$ alkyl radical, $R_1$ and $R_2$ can occupy any position on the benzofuran ring provided that when $R_1$ and $R_2$ both denote an alkyl radical, they do not occupy the positions 2 and 3 at the same time, the concentration of the hydroxybenzofurans of formula (I) being 0.05 to 3.5% by weight of the total weight of the composition, an oxidizing agent being present in the composition applied in the second stage, or the oxidizing agent being applied to the hair itself in a third stage, allowing it to act for 10 to 40 minutes, and then rinsing the hair, washing it with shampoo, rinsing it again and drying it.

* * * * *